United States Patent
Schaldach et al.

(10) Patent No.: US 6,501,986 B1
(45) Date of Patent: Dec. 31, 2002

(54) IMPLANTABLE DEFIBRILLATOR

(75) Inventors: Max Schaldach, Erlangen (DE); Sven Poga, Muenster (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 231 days.

(21) Appl. No.: 09/721,553

(22) Filed: Nov. 22, 2000

(30) Foreign Application Priority Data

Nov. 23, 1999 (DE) .......................... 199 57 481

(51) Int. Cl.⁷ .................................. A61N 1/39
(52) U.S. Cl. ................................. 607/5; 607/7
(58) Field of Search ......................... 607/5, 7, 60, 62

(56) References Cited

U.S. PATENT DOCUMENTS

| | | | |
|---|---|---|---|
| 5,002,052 A | | 3/1991 | Haluska |
| 5,269,298 A | * | 12/1993 | Adams et al. .................. 607/5 |
| 5,441,519 A | * | 8/1995 | Sears ............................. 607/5 |
| 5,470,342 A | * | 11/1995 | Mann et al. .................... 607/13 |
| 5,486,198 A | * | 1/1996 | Ayers et al. .................. 600/518 |
| 5,531,767 A | * | 7/1996 | Fain ............................... 607/5 |
| 5,554,174 A | * | 9/1996 | Causey, III ................... 607/5 |
| 5,609,618 A | | 3/1997 | Archer |
| 5,674,248 A | * | 10/1997 | Kroll et al. .................... 607/5 |
| 5,861,006 A | | 1/1999 | Kroll |
| 5,891,169 A | * | 4/1999 | Boheim et al. ................ 607/4 |
| 5,899,923 A | | 5/1999 | Kroll et al. |
| 5,959,371 A | * | 9/1999 | Dooley et al. ............... 307/125 |
| 6,070,099 A | | 5/2000 | Magin |
| 6,115,633 A | | 9/2000 | Lang et al. |
| 6,128,531 A | * | 10/2000 | Campbell-Smith ............. 607/5 |

FOREIGN PATENT DOCUMENTS

| | | |
|---|---|---|
| DE | 42 31 603 A1 | 3/1994 |
| DE | 689 21 948 T2 | 3/1995 |
| DE | 196 54 494 A1 | 5/1998 |
| EP | 0 806 222 A2 | 11/1997 |
| EP | 0 916 365 A1 | 5/1999 |

* cited by examiner

Primary Examiner—Michael Powell Buiz
Assistant Examiner—Ramesh Krishnamurthy
(74) Attorney, Agent, or Firm—Hahn Loeser + Parks LLP; Stephen L. Grant

(57) ABSTRACT

The invention concerns an implantable defibrillator (1) comprising a chargeable voltage source (2) and a pulse generator (3) which is formed from a voltage multiplier (5) and a capacitor (4) chargeable to the defibrillation voltage. Provided between the capacitor (4) and the voltage source (2) is a line connection (6) by way of which electrical energy which has not been consumed or which is not required for the tissue stimulation procedure can be returned from the capacitor to the voltage source.

11 Claims, 2 Drawing Sheets

IMPLANTABLE DEFIBRILLATOR

TECHNICAL FIELD

The invention concerns an implantable defibrillator comprising a chargeable voltage source with a long service life and a pulse generator having a capacitor which is chargeable, preferably by way of a voltage multiplier.

BACKGROUND

For the purposes of charging up the capacitor a sufficiently large amount of energy is taken from the voltage source in order and if necessary to be able to deliver a defibrillation current pulse into the tissue to be stimulated by means of the pulse generator by way of cardiac electrodes which are connected to the capacitor terminals. The amount of energy of such a direct current surge in pulse form which is to be applied in the case of ventricular fibrillation is in the range of between 50 and 500 Ws with a pulse duration in the ms-range.

European patent application EP 0 916 365 A1 and U.S. Pat. No. 5,609,618 disclose defibrillators of that kind, wherein the voltage multiplier is in the form of a DC-DC-current transformer.

In order to achieve reliable operational management for a defibrillator, sensor means are provided in order to be able to already initiate charging of the capacitor of the pulse generator upon the occurrence of tissue conditions which on the basis of experience are to be assessed as initial symptoms of early cardiac fibrillation so that if necessary the capacitor has already received the amount of energy which is required for the direct current pulse.

In the event that cardiac fibrillation fails to occur that amount of energy has to be removed internally if the defibrillator is not activated in accordance with the prevailing safety requirements, as discussed in EP 0 916 365 A1. Energy losses which occur as a result disadvantageously lead to a premature reduction in the performance and capability of the battery so that replacement of the defibrillator by re-implantation has to take place at a correspondingly earlier moment in time.

SUMMARY

In consideration of the deficiencies in the state of the art therefore the object of the present invention is to provide a defibrillator of the general kind set forth in the opening part of this specification, having an improved circuitry design which permits particularly energy-economical operation of the defibrillator in order to achieve an increase in the length of the change cycle of the defibrillator by virtue of an increase in the service life of the voltage source.

In accordance with the invention that object is attained by a defibrillator of the kind set forth in the opening part of this specification, with a return line between the capacitor and the voltage source which is of such a nature that electrical energy which is not consumed or which is not required for tissue stimulation can be returned by way of the return line from the capacitor to the voltage source.

The invention involves the realisation that energy can be stored in a rechargeable battery if there is applied to the battery a voltage which is of a greater value than the terminal voltage which exists at the battery at the present time. Thus it is possible for example for energy in the form of an electrical charge stored in a capacitor to be returned to a battery if the capacitor voltage exceeds the terminal voltage of the battery.

In accordance with a preferred embodiment of the invention, in the case of a defibrillator which is implanted for the stimulation of human cardiac tissue, there is provided a return line between the capacitor and the voltage source in the form of a chargeable batter, by way of which electrical energy which is not consumed or which is not required for tissue stimulation is returned from the capacitor to the battery. In that way, the capacity and performance of the battery can advantageously be improved and the service life thereof can be prolonged so that replacement of the defibrillator by re-implantation because of the battery being exhausted has to be implemented only at a later time, which is particularly desirable for the patient in question.

In accordance with an advantageous development of the invention, in the case of the defibrillator a switching device is arranged in the return line in order to be able to easily control in respect of time the return of energy to the battery from the capacitor which is charged up to the high voltage required for defibrillation. A control option of that kind is required as the operational management of the defibrillator may not be adversely affected by the return line and the return flow of energy may occur only when it is reliably established with certainty that tissue stimulation is no longer necessary.

In accordance with the preferred embodiment of the invention the switching device which is disposed in the return line is adapted to be activatable by a clock generator. Upon actuation the clock generator produces an output voltage in pulse form, wherein a time window is delimited by the pulses. The size of the time window is so selected that it is certain to involve a time region which extends at least from the moment in time at which sensor means are operable to detect a condition of the tissue in which—in accordance with empirical values—tissue stimulation will be required with a very high degree of probability in a short time to the moment in time when tissue stimulation—if necessary—has been concluded.

If the moment in time intended for tissue stimulation has passed and no tissue stimulation has been triggered off, then the switching device in the return line is activated. The connection between the capacitor and the battery is made and the amount of energy which has not been consumed is fed into the battery.

A separate control is provided for co-ordination of activation of the clock generator for controlling the switching device in the return line, and switching on the pulse generator for producing the capacitor charge which is required for a tissue stimulation procedure which is possibly to be implemented. The signal input of that control is connected to sensor means which are positioned in the tissue to be stimulated and by which the condition of the tissue is continuously monitored. The signal outputs of the control are connected to the pulse generator and to the clock generator so that, upon the occurrence of sensor signals involving corresponding signs of tissue stimulation becoming necessary in a short time, activation of the pulse generator and the clock generator is effected at the same time. The clock generator in turn activates the switching device in the energy return line, in which case the energy return line is interrupted by the first pulse which delimits the time window of the clock generator so that charging of the capacitor in the pulse generator can take place.

If, after a time which is defined by the second pulse of the time window of the clock generator, no tissue stimulation takes place, for example because the cardiac tissue has stabilised itself, then the switching device in the energy return line is activated again by the second pulse of the time window and restores the line connection between the battery and the capacitor terminal.

In accordance with an advantageous development of the invention, a time delay member is provided in the control line connecting the pulse generator to the signal output of the control, in order in a simple manner to provide that the energy return line is certain to be interrupted before charging of the capacitor to a voltage level which is required for the direct current pulse begins.

In accordance with an advantageous variant of the invention, for the time window which embraces at least a region from the moment in time at which the pulse generator is switched on to the theoretical moment in time at which a required tissue stimulation procedure is triggered off, there is provided a safety time range which is of a value of at least 10% of the minimum time window required.

Another advantageous variant of the invention provides for using a telemetrically programmable clock generator in order conveniently to be able to implement patient-specific adjustment of the time window.

Other advantageous developments of the invention are characterised in the appendant claims or are set forth in greater detail hereinafter together with the description of the preferred embodiment of the invention with reference to the drawing in which:

DETAILED DESCRIPTION OF THE INVENTION

Figure 1:
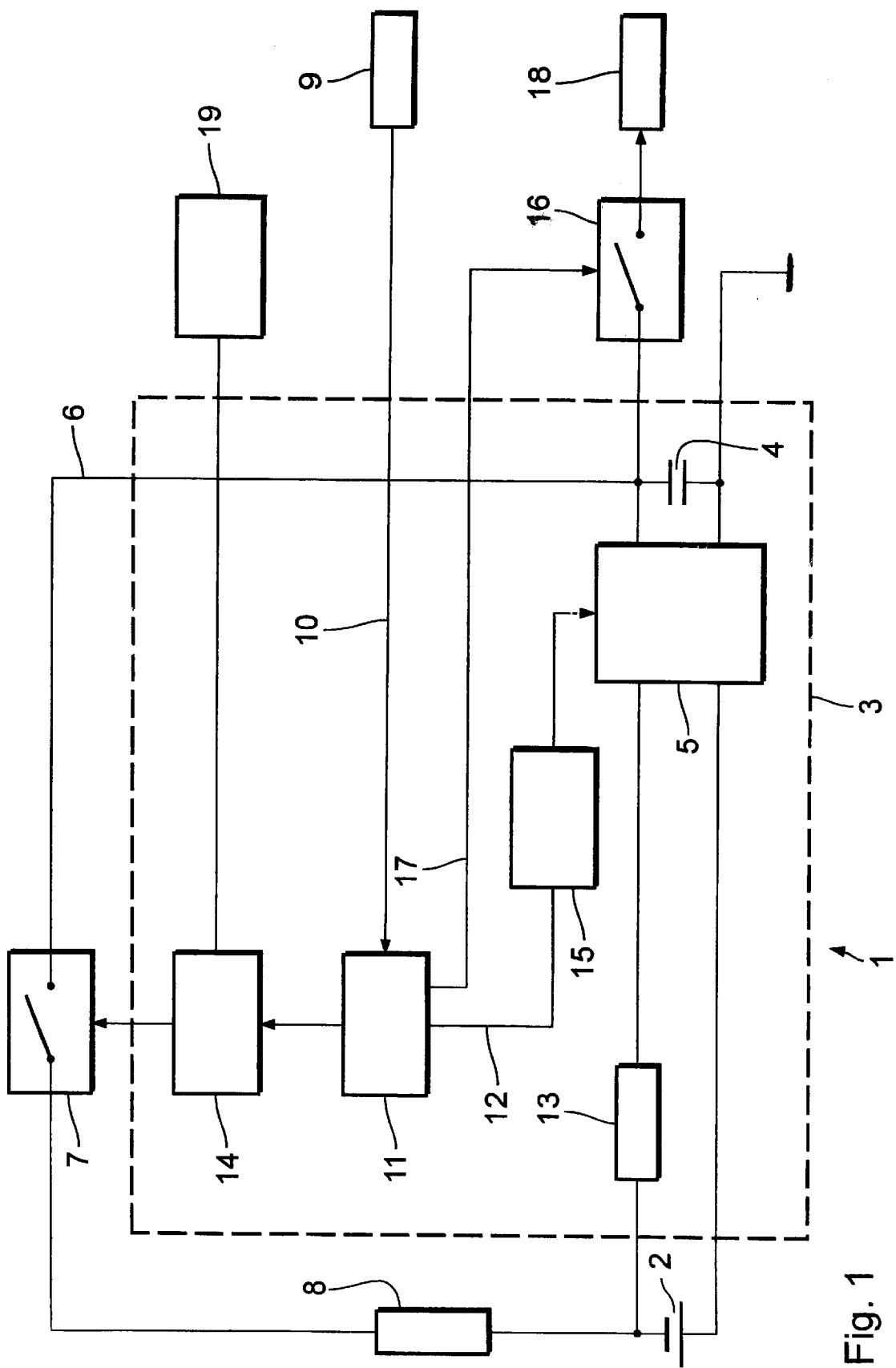
FIG. 1 shows a preferred embodiment of the invention in the form of a block circuit diagram.

The implantable defibrillator 1, the block circuit diagram of which is shown in FIG. 1, has a voltage generator 3 which is fed by a rechargeable battery 2. The capacitor 4 of the pulse generator 3 is charged up to a high voltage by the battery 2 by way of a voltage multiplier 5 in order and if necessary to be able to deliver a voltage surge for the stimulation of cardiac tissue.

The capacitor 4 is connected to the positive terminal of the battery 2 by an energy return line 6 in which a switch 7 and a series resistor 8 are arranged. When the capacitor 4 is charged up, the stored energy can be returned to the battery 2 by closure of the switch 7, in the event that stimulation of the cardiac tissue is superfluous.

The condition of the cardiac tissue which is possibly to be stimulated is detected by electrodes 9 which are connected by way of an electrode line 10 to an electronic control unit 11. The control unit 11 by way of its output line 12 activates the voltage multiplier 5 connected to the battery 2 by way of a series resistor 13 if its signal input is actuated by way of the electrode line 10 by a signal which is detected whenever the cardiac tissue is in a condition in which ventricular fibrillation is to be expected in a relatively short time and defibrillation by a dc voltage surge will be required with a very high degree of probability.

In order to ensure that the capacitor 4 of the pulse generator 3 can be charged up to the voltage level required for the defibrillation procedure, a clock generator 14 is simultaneously activated by the control unit 11. A pulse voltage in the form of a time window delimited by two voltage pulses is available at the signal output of the clock generator 14. The first voltage pulse of the time window opens the switch 7 in the energy return line 6 in order to interrupt the direct connection between the battery and the capacitor.

The provision of a delay member 15 in the output line 12 of the control unit 11 provides that the voltage multiplier, for charging up the capacitor 4, is switched on only after the return line 6 has been interrupted.

If a cardiac tissue condition which requires defibrillation is detected by the sensor electrodes, the defibrillator 1 provides for the delivery of a direct current pulse surge after activation of a switch 16 by a switching signal on the output line 17 of the control unit 11. The defibrillation electrode is identified by reference numeral 18.

As secure empirical values are available for the period of time for the occurrence of the initial symptoms of possible ventricular fibrillation of the heart and the onset of ventricular fibrillation, there is selected for the width of the time window produced by the clock generator 14 (see reference 21 in FIG. 2), a value which corresponds at least to the time from the moment of detection of an initial early symptom of ventricular fibrillation to be expected, to the time at which ventricular fibrillation actually starts. The size of the time window which can be produced by the clock generator 14 is adjustable and is programmed in the case of the implanted defibrillator by a telemetry device 19.

The second voltage pulse which is delivered by the clock generator 14 and which defines the end of the time window closes the switch 7 in the energy return line 6 and the energy which is not required for the defibrillation procedure flows back to the battery 2, with the capacitor 4 being discharged.

Figure 2:
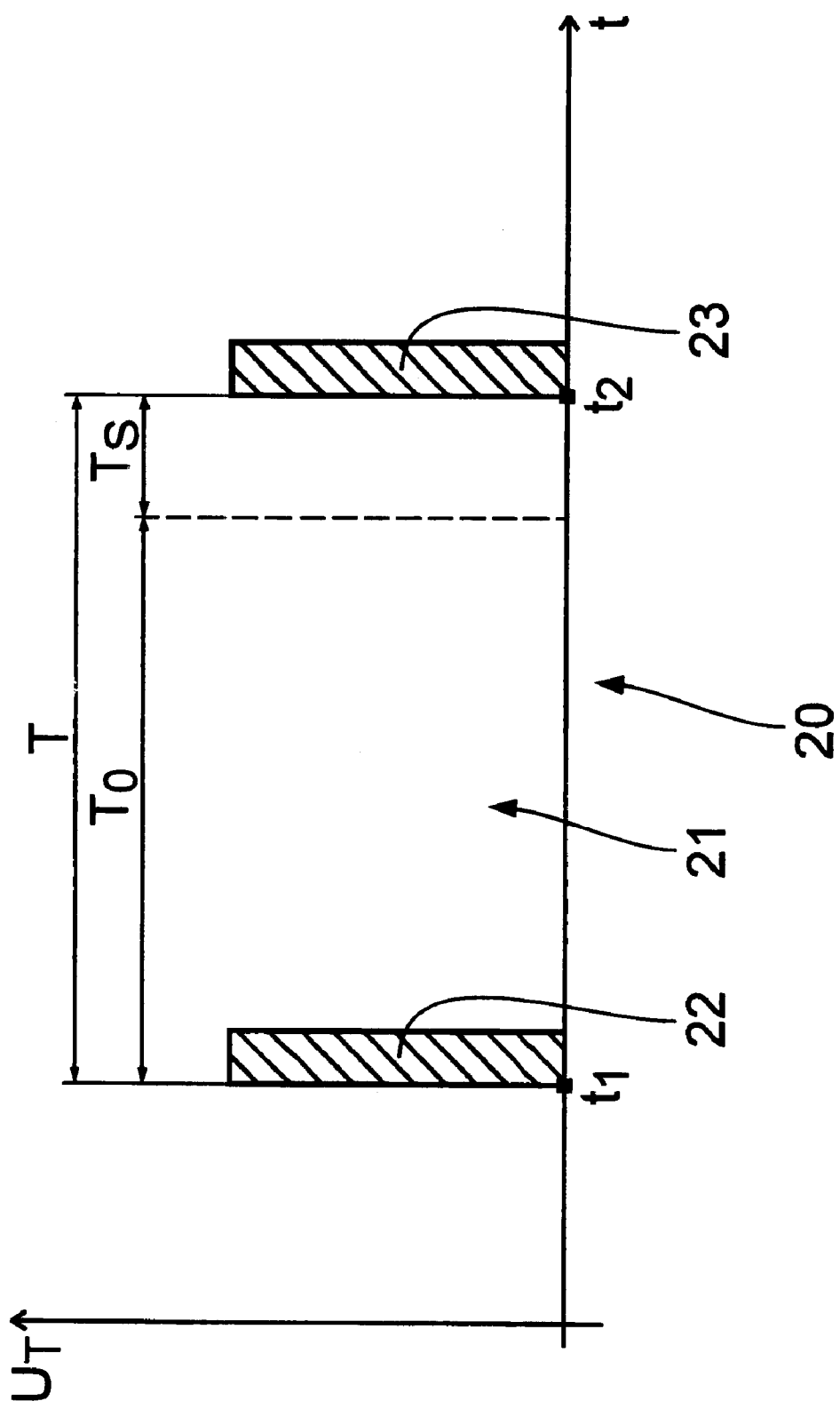
FIG. 2 shows the pulse diagram of a clock generator shown in the block circuit diagram of FIG. 1.

The diagram 20 shown in FIG. 2 illustrates the pattern in respect of time of the output voltage $U_T$ of the clock generator 14 shown in FIG. 1. The length $T=t_1-t_2$ of the time window 21 is defined by the leading edges of the pulses 22 and 23 which are produced by the clock generator. For safety reasons, a time region $T_s$ is provided in the time window 21. The extension of the time region $T_o$ of the time window 21, which is determined by the moment in time between detection of the initial symptoms of possible occurrence of ventricular fibrillation and the moment in time of detection of actually occurring ventricular fibrillation compensates for possible patient-specific tolerances in respect of that time region. This ensures that the return of energy stored in the capacitor of the pulse generator or a residual amount of energy to the battery (see references 2, 3 and 4 in FIG. 1) occurs only if ventricular fibrillation has failed to materialise and will not occur again in the near future or stimulation of the cardiac tissue was implemented by virtue of ventricular fibrillation.

As the clock generator 14 is adapted to be telemetrically programmable the medical empirical values in respect of the time between detection of the early symptoms of possible ventricular fibrillation and the moment in time of the actual onset of ventricular fibrillation can be taken into account, with patient-specific particularities, without entailing particular trouble and effort, for the purposes of establishing the optimum time window of the clock generator.

The invention is not limited in terms of implementation thereof to the above-described preferred embodiments. On the contrary a number of alternative configurations are possible, which make use of the illustrated structure even in configurations of a basically different kind.

What is claimed is:

1. An implantable defibrillator for stimulating cardiac tissue by emitting a pulse within a time region defined as a time at which an initial early symptom of fibrillation is sensed to a time when the pulse may be needed to stimulate the tissue, the defibrillator comprising:

a chargeable voltage source;

a pulse generator, the pulse generator comprising a voltage multiplier and a capacitor, wherein the capacitor is chargeable to a voltage required for defibrillation;

a return line between the capacitor and the voltage source, said return line configured such that electrical energy not used in tissue stimulation is returned from the capacitor to the voltage source thereby.

2. A defibrillator as set forth in claim 1 wherein the return line is adapted to be interrupted by a switching device.

3. A defibrillator as set forth in claim 1 wherein the pulse generator further comprises a clock generator for activation of the switching device.

4. A defibrillator as set forth in claim 3 further comprising a control which is connected to a sensor means wherein the sensor means is arranged in the cardiac tissue to be stimulated, and wherein the control activates the voltage multiplier and the clock generator when the sensor means detects the initial symptom of fibrillation.

5. A defibrillator as set forth in claim 4 wherein the activated clock generator produces a time window, after the expiry of which a connection is made between the capacitor and the voltage source by the switching device.

6. A defibrillator as set forth in claim 3 characterised in that the clock generator is adapted to be telemetrically programmable.

7. A defibrillator as set forth in claim 5 wherein the clock generator produces a first voltage pulse and a second voltage pulse, each said voltage pulse having a leading edge and a trailing edge, wherein the first voltage pulse is produced when the sensor detects the initial early symptom of fibrillation and activates the clock generator, and wherein the second voltage pulse is produced at the end of the time window.

8. A defibrillator as set forth in claim 7 wherein the time window is at least the length of time of the time region, and is defined as the time between the leading edge of the first voltage pulse and the leading edge of the second voltage pulse.

9. A defibrillator as set forth in claim 8 wherein the time window further comprises a safety time region, such that the time window exceeds the time region by at least ten percent.

10. A defibrillator as set forth in claim 4 wherein the control further comprises an output line connecting the control to the voltage multiplier of the pulse generator.

11. A defibrillator as set forth in claim 7 further comprising a time delay means arranged in the output line.

* * * * *